(12) United States Patent
Koch

(10) Patent No.: US 10,018,577 B2
(45) Date of Patent: Jul. 10, 2018

(54) METHODS AND SYSTEMS FOR IMAGING BULK MOTIONAL VELOCITIES IN PLASMAS

(71) Applicant: National Security Technologies, LLC, Las Vegas, NV (US)

(72) Inventor: Jeffrey A. Koch, Livermore, CA (US)

(73) Assignee: Mission Support and Tests Services, LLC, North Las Vegas, NV (US)

( * ) Notice: Subject to any disclaimer, the term of this patent is extended or adjusted under 35 U.S.C. 154(b) by 177 days.

(21) Appl. No.: 15/090,408

(22) Filed: Apr. 4, 2016

(65) Prior Publication Data

US 2016/0290939 A1    Oct. 6, 2016

Related U.S. Application Data

(60) Provisional application No. 62/142,985, filed on Apr. 3, 2015.

(51) Int. Cl.
  *G21K 1/06*    (2006.01)
  *G01N 23/207*  (2018.01)

(52) U.S. Cl.
  CPC ... *G01N 23/2076* (2013.01); *G21K 2201/062* (2013.01)

(58) Field of Classification Search
  CPC ........ G01N 23/06; G01N 23/207; G21K 1/06; G21K 1/02
  See application file for complete search history.

(56) References Cited

U.S. PATENT DOCUMENTS

| | | | |
|---|---|---|---|
| 3,032,656 A | 5/1962 | Hosemann et al. |
| 4,426,719 A | 1/1984 | Fraenkel |
| 4,780,899 A | 10/1988 | Adema et al. |
| 4,949,367 A | 8/1990 | Huizing et al. |
| 6,236,710 B1 | 5/2001 | Wittry |
| 6,259,763 B1 | 7/2001 | Bitter et al. |
| 6,317,483 B1 | 11/2001 | Chen |
| 2002/0003662 A1 | 1/2002 | Marcelli et al. |
| 2012/0256332 A1 | 10/2012 | Maj et al. |
| 2013/0108022 A1 | 5/2013 | Kugland et al. |

OTHER PUBLICATIONS

Ince-Cushman et al.; "Spatially resolved high resolution X-ray spectroscopy for magneticlaly confined fusion plasmas" Reviwe of Scientific Instruments 79, (2008).*

U.S. Appl. No. 15/073,946, filed Mar. 18, 2016, Jeffrey A. Koch, et al.

(Continued)

*Primary Examiner* — Courtney Thomas
(74) *Attorney, Agent, or Firm* — Weide & Miller, Ltd.

(57) ABSTRACT

A method and apparatus for imaging the distribution of bulk motional velocities in plasmas such as inertial confinement fusion (ICF) implosions. This method and apparatus use multiple narrow-band x-ray crystal imaging systems, one or more of which have a bandpass tuned to lie within the Doppler-broadened emission line profile of a suitable plasma emission line. Crystals tuned on the one end of the profile will preferentially reflect x-rays from plasma ions moving towards the crystals, while crystals tuned to another end of the profile will preferentially reflect x-rays from plasma ions moving away from the crystals.

18 Claims, 5 Drawing Sheets

(56) References Cited

OTHER PUBLICATIONS

"High-energy x-ray microscopy techniques for laser-fusion plasma research at the Nation Ignition Facility", Jeffrey A. Koch, et al., Applied Optics, vol. 37, No. 10, Apr. 1, 1998, 12 pages.

"4.5- and 8-keV emission and absorption x-ray imaging using spherically bent quartz 203 and 211 crystals (invited)", Review of Scientific Instruments, vol. 74, No. 3, © 2003 American Institute of Physics, Plasma Diagnostics, Mar. 2003, 6 pages.

"Time-resolved ten-channel monochromatic imaging of inertial confinement fusion plasmas", Ingo Uschmann, et al., Applied Optics, vol. 39, No. 31, Nov. 1, 2000.

"Compact imaging Bragg spectrometer for fusion devices", Bertschinger, G., et al., Review of Scientific Instruments, Oct. 2004, vol. 75, No. 10, ISSN: 00346748; DOI: 10.1063/1.1781755, http://scitation.aip.org/content/aip/journal/rsi/75/10/10.1063/1.1781755, http://www.researchgate.net/publication/30047872_Compact_imaging_Bragg_spectrometer_for_fusion_devices/file/3deec528dd4lcla2d2.pdf, (c) 2004 American Institute of Physics, Oct. 2004, 3 pages.

"X-ray instrumentation for protein crystallography with SR", Popov, A.N., et al., E.G., Review of Scientific Instruments, vol. 63, No. 1, pt.11B, 1031, ISSN: 0034-6748; DOI: 10.1063/1.1143190; (c) 1992 American Institute of Physics, , Jan. 1992, 2 pages.

"Experimental observation of two-dimensional focusing of X-rays in backscattering", Kushnir, V.I., et al., JETP Letters, vol. 48, No. 2, pp. 117-119, ISSN: 0021-3640, Jul. 1988, 3 pages.

"Primary extinction and absorption: a theoretical approach based on the Takagi-Taupin equations. Application to spherical crystals", Chukhovskii, F. N., et al., Acta Crystallographica, Section A (Foundations of Crystallography), vol. 54, No. 2, 191-198, ISSN: 0108-7673, DOI: 10.1107/S0108767397012579, Mar. 1, 1998, 8 pages.

"Bent crystal selection and assembling for the LAUE project", Liccardo, et al., Proceedings of SPIE—The International Society for Optical Engineering, v 8861, 2013, Optics for EUV, X-Ray, and Gamma-Ray Astronomy VI, ISSN: 0277786X, E-ISSN: 1996756X, ISBN-13: 9780819497116; DOI: 10.1117/12.2023617, Oct. 1, 2013, 9 pages.

"Bent crystal analyzer without grooves for inelastic X-ray scattering", Kushnir, et al., Review of Scientific Instruments, vol. 67, No. 9. [+CD-ROM], 5 pp., ISSN: 0034-6748, Sep. 1996, 10 pages.

"Bent crystals by surface grooving method for high-efficiency concentration of hard x-ray photons by a Laue lens", Guidi, et al., Proceedings of SPIE—The International Society for Optical Engineering, vol. 8147, 2011, Optics for EUV, X-Ray, and Gamma-Ray Astronomy V, ISSN: 0277786X, ISBN-13: 9780819487575, DOI: 10.1117/12.895334, Oct. 11, 2011, 3 pages.

"Johansson crystals for x-ray diffractometry and demanding spectroscopy applications", Verman, Boris, et al., Proceedings of SPIE—The International Society for Optical Engineering, vol. 8139, 2011, Advances in X-Ray/EUV Optics and Components VI, ISSN: 0277786X, ISBN-13: 9780819487490, DOI: 10.1117/12.893739, Sep. 28, 2011, 1 page.

"Curved crystals for high-resolution focusing of X and gamma rays through a Laue lens", Guidi, et al., Nuclear Instruments &, Methods in Physics Research, Section B (Beam Interactions with Materials and Atoms), vol. 309, 249-253, ISSN: 0168-583X, DOI: 10.1016/j.nimb.2013.01.070, Aug. 15, 2013, 2 pages.

"X-ray crystal devices for measuring compression and stability of laser fusion targets. Final report", Post, B., Sponsor: Department of Energy, Washington, DC.; Report: DOE/DP/10697-T1, 42p, May 1990, 1 page.

"Large aperture point-focusing diffractor for X rays", Wittry, D.B., et al, Applied Physics Letters, vol. 52, No. 17, 1381-1382, ISSN: 0003-6951, DOI: 10.1063/1.99122, Apr. 25, 1988, 2 pages.

"Imaging with Spherically Bent Crystals or Reflectors" M. Bitter, et al., IOP Publishing, Journal of Physics B: Atomic Moleculor and Optical Physics, 43 (2010) 144011 (8pp) DOI: 10.1088/0953-4075/43/14/144011, stacks.iop.org/JPhysB/43/144011, Jul. 5, 2010, 9 pages.

\* cited by examiner

METHODS AND SYSTEMS FOR IMAGING BULK MOTIONAL VELOCITIES IN PLASMAS

STATEMENT REGARDING FEDERALLY SPONSORED RESEARCH OR DEVELOPMENT

This invention was made with government support under Contract No. DE-AC52-06NA25946 and was awarded by the U.S. Department of Energy, National Nuclear Security Administration. The government has certain rights in the invention.

BACKGROUND

A plasma is one of the four fundamental states of matter, the others being solid, liquid, and gas. Plasma behavior may be extraordinarily varied and subtle. In particular, hydrodynamic motion in imploding plasmas is not well diagnosed at all relevant spatial scales. It has been theorized that bulk macroscopic motion can be imparted to regions of imploding plasmas by three-dimensional effects, serving as a sink for energy that would otherwise go towards heating the plasma. However, there has been no ability to directly diagnose such motion.

It is known that astronomers utilize Doppler shifted electromagnetic radiation emission as a diagnostic of material motion in space. This is typically a direct time-domain frequency measurement in the radio region of the spectrum, and measures line-of-sight velocities in objects such as nebulae and galaxies Likewise, Doppler shift analysis of sound and light waves is known.

SUMMARY

To overcome drawbacks in the prior art, proposed is plasma analysis using Doppler shift principles. This diagnostic capability will benefit in-laboratory plasma analysis, such as for example, but not limited to, inertial confinement fusion (ICF), where analyzing ignition behavior (such as for example at the National Ignition Facility (NIF)) has been attributed in various venues to transfer of implosion energy to (unseen and undiagnosed) bulk rotational motion. However, laboratory plasmas are small and extremely hot and thus pose challenges for accurate diagnosed by radio-frequency measurements of Doppler shifts. To overcome the drawbacks of the prior art, it has been found that spectral-domain measurements of Doppler wavelength shifts are practical, and can be extended to imaging diagnostics if the imaging system spectral bandpass is small.

Proposed is to utilize near-normal-incidence, spherical or ellipsoidal imaging crystals as narrowband x-ray imaging systems for diagnosis of bulk motion in laboratory plasmas such as ICF implosions. An array of imaging crystals, one or more of which have a bandpass that is narrow compared with the Doppler profile of a suitable plasma emission line, or narrower than the Doppler profile of a suitable plasma emission line are proposed for use. One or more of the imaging crystal are tuned to a slightly different part of the Doppler profile, to generate an array of quasi-monochromatic images. The crystals tuned to predetermined ions within the plasma emission lines will produce monochromatic images that are brighter in certain regions which are emitting x-rays that are reflected and detected by a particular detector. By combining the monochromatic images from the crystals tuned to wavelengths or ions within the plasma emission lines, it can be determined where the plasma is moving and which sections of the plasma are moving towards or away from the crystals, and a color-coded map of bulk motion within the plasma may be reconstructed from the monochromatic images.

The technology for producing images using crystals is known (e.g. E. Forster et al., Laser Particle Beams 9, 135 (1991)), but this particular application, arrangement, and type of array of crystals is novel. The instrument could, in one embodiment, be a 10-channel system built for electron temperature measurements of implosion plasmas at Osaka University (I. Uschmann et al., Applied Optics 39, 5865 (2000)). However this system would not function for the purpose of the intended innovation because the bandpass of each crystal is too wide, and the wavelength separation of the different bands is incorrect, since this application benefits from monochromatic imaging within the Doppler-broadened profile of a single emission line, rather than in widely separated bands viewing different emission lines.

Other applications include analysis of larger, cooler plasmas. Furthermore, the same method and apparatus could work in absorption using a large broadband backlight, potentially allowing diagnosis of bulk motion in explosives-driven implosions.

In summary, disclosed is a novel method and apparatus for imaging the distribution of bulk motional velocities in plasmas such as inertial confinement fusion (ICF) implosions. This innovation uses multiple narrow-band x-ray crystal imaging systems, one or more of which have a bandpass tuned to lie within the Doppler-broadened emission line profile of a suitable plasma emission line. Crystals tuned on the one end of the profile will preferentially reflect x-rays from plasma ions moving towards the crystals, while crystals tuned to another end of the profile will preferentially reflect x-rays from plasma ions moving away from the crystals. Software analysis may produce images which have or show a color-coded map of bulk motional velocities. This is an important measurement capability that does not currently exist, and could have an enormous impact on ICF progress at facilities such as the National Ignition Facility (NIF). Many other applications can also be envisioned for other application for high-energy-density physics (HEDP) and test facilities.

It is further contemplated that the method may process simulated data from a realistic (3D) simulation of an implosion plasma. It is also contemplated that refinement of the design parameters to adjust various factors may occur, such as the crystal or aperture dimensions, without departing from the scope of the innovation. In one or more embodiments, the method and apparatus is configured for use with backlit absorption imaging of cold plasmas, such as but not limited to explosive-driven implosions.

A system is disclosed herein for detecting bulk motional velocities in a plasma that includes a crystal array comprising at least two crystalline reflectors such that the reflectors are tuned to reflect x-rays of a particular wavelength within a single emission band from the plasma to create reflected x-rays. The system also includes two or more detectors configured to receive reflected x-rays and generate detector output such that each detector is associated with a x-ray wavelength and the detector output is combinable to represent a bulk material velocity of the plasma.

In one embodiment the two or more detector comprises film. The angle defined by the one of the at least two crystalline reflectors and an x-ray path reflected from a crystalline reflector to one of the two or the one or more detectors is between 80 and 90 degrees. It is contemplated that the system further comprises at least one shield disposed between a plasma being observed and the two or more detectors. The system may further comprise a processing device, at least one memory, and a display such that the processing device is configured to execute machine readable instructions stored on the memory, which when executed, cause the system to receive data from the detector. The data comprises information for monochromatic images corresponding to x-rays reflected by the at least two crystalline reflectors and then process the data to individually code the monochromatic images and overlay the monochromic images to produce a composite image such that the composite image shows Doppler shifts within the single emission band.

In one embodiment, the system further comprises a collimator configured to narrow a beam of the x-rays that are reflected by the crystal array, slits configured to control the divergence of the x-rays, and at least one filter configured to block or filter out one or more wavelengths or energy bands in the x-ray spectrum.

Also disclosed is a method for detecting bulk motional velocities in a plasma. This exemplary method comprises identifying a predetermined x-ray emission band emanating from the plasma, tuning two or more crystalline reflectors within a crystal array to reflect x-rays within the predetermined emission band, reflecting the x-rays from the plasma onto a detector such that the detector comprises one or more detectors. The method then generates monochromatic images corresponding to the x-rays reflected by the two or more crystalline reflectors and combines the monochromatic images into a composite image to identify bulk motional velocities within the plasma.

In one embodiment, the two or more crystalline reflectors have a bandpass that is narrow compared with a Doppler profile of the emission band. The detector(s) may comprises at least one of an image plate; a CCD, CMOS, an N-type metal-oxide-semiconductor, or other image sensor camera; film; photographic film; or a gated micro channel plate detector. The combining step may include color coding the monochromatic images. In one configuration, the two or more crystal reflectors reflect x-rays emanating from the plasma at different orientations with respect to the plasma. The meridional plane of plane of the crystalline reflectors may be set at the equatorial plane of the plasma.

Also disclosed is a system for detecting bulk motional velocities in a plasma and this system include a crystal array tuned to reflect x-rays having a predetermined emission line, one or more detectors configured to detect x-rays reflected from the crystal array, one or more shields configured to block the one or more detectors from x-rays emanating directly from the plasma, and a processor configured to receive image information from the one or more detectors. The image information comprises monochromatic images of the x-rays reflected by the crystal array and the processor is also configured to combine the monochromatic image into a composite image showing Doppler shifts within the emission line.

In one variation, the crystal array comprises two or more crystalline reflectors tuned to different center wavelengths about a center wavelength of a profile of the predetermined emission line. A created composite image may be a color coded image of the monochromatic images overlaid on top of each other. The angle defined by the one of the crystalline reflectors and an x-ray path reflected from the one crystalline reflector to the one or more detectors is between 80 and 90 degrees. It is contemplated that the system may further comprise a collimator configured to narrow a beam of the x-rays that are reflected by the crystal array, slits configured to control the divergence of the x-rays, and at least one filter configured to block or filter out one or more wavelengths or energy bands in the x-ray spectrum.

Other systems, methods, features and advantages of the invention will be or will become apparent to one with skill in the art upon examination of the following figures and detailed description. It is intended that all such additional systems, methods, features and advantages be included within this description, and be within the scope of the invention. While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

DETAILED DESCRIPTION OF EMBODIMENTS

Figure 1:
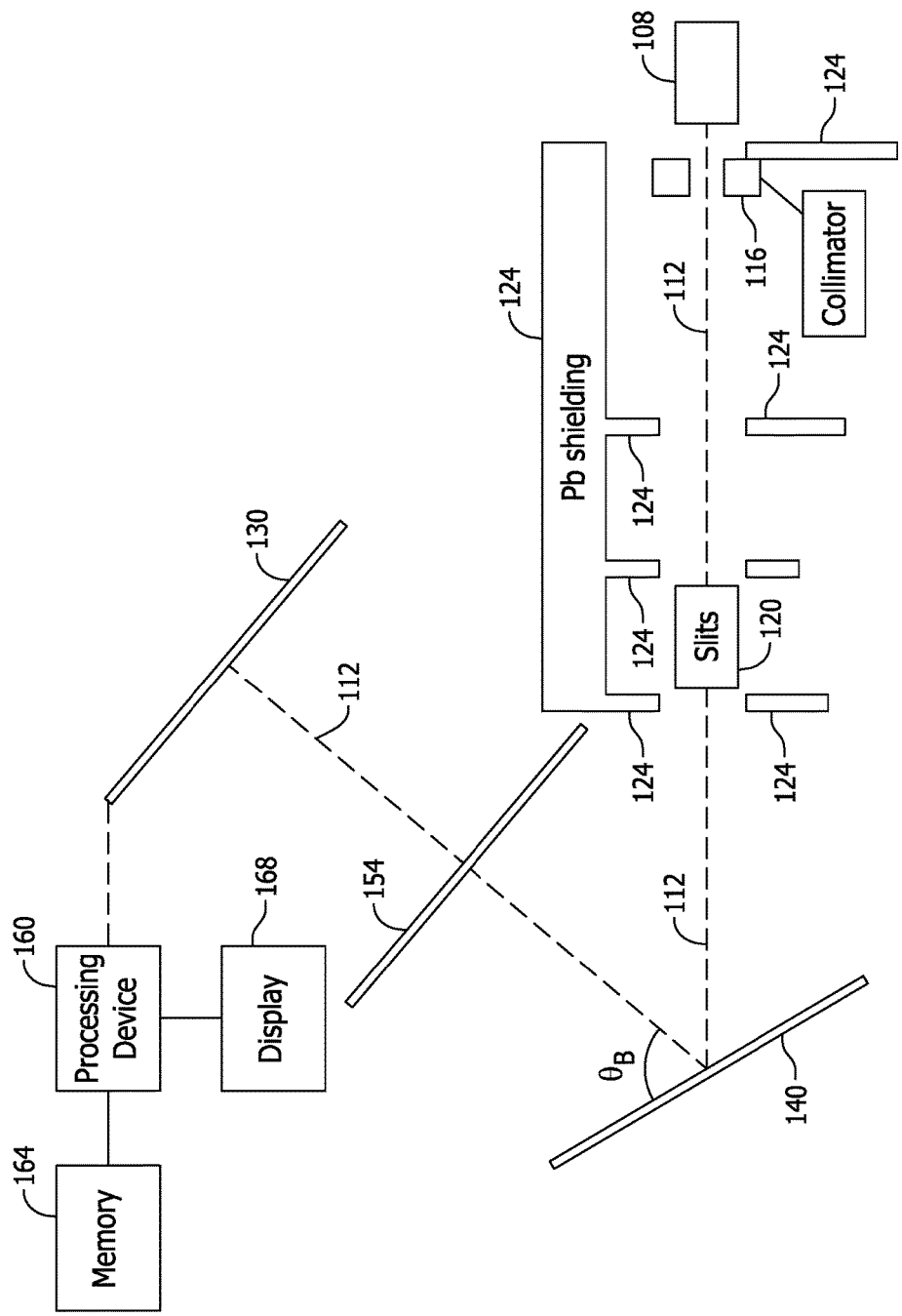
FIG. 1 is a block diagram illustrating an example system for imaging bulk motional velocities in plasmas according to one embodiment.

FIG. 1 is a block diagram illustrating an example system for imaging bulk motional velocities in plasmas. This is but one possible configuration and as such, one or more elements of FIG. 1 may be substituted with or replaced by other elements, as described below or as understood by one of ordinary skill in the art, without departing from the scope of the invention. As discussed below, the source of the x-rays may vary based on application and the detector may vary based on the application and nature of imaging.

Turning now to FIG. 1, a source 108 is shown which directs energy or any emissions, such as x-rays on an x-ray path 112 to a detector 130 after reflection by an array of two or more crystals 140. Although shown as a single path, it is contemplated that multiple paths may be present in this and other embodiments. The crystals in the array 140 could be flat, spherical, or ellipsoidal. In this embodiment, the source 108 may be an Ag based x-ray source. In one example, Ru or Ag He-$\alpha$ imaging of burning inertial confinement fusion cores may serve as the source, or any type plasma that emit x-ray radiation, subject to the Bragg condition being met for the crystal array 140 and x-ray wavelength relationship. The source 108 may comprise any type of event that emits x-ray radiation, such as a plasma.

An x-ray path 112 emanates from the source 108. The x-ray path passes through an optional collimator 116. The collimator 116 is a known device and is configured to narrow a beam of particles or waves to cause the x-rays to become more aligned in a specific direction or to cause the spatial cross-section of the x-rays to become smaller. After the x-ray path 112 passes through the collimator 116, the path enters or passes through one or more slits 120 configured to control or establish the divergence of the x-ray beam. Slits 120 are generally known by one of ordinary skill in the art and as such are not described in detail herein. Slits 120 or an equivalent may be purchased from Newport® Inc. located in Irvine, Calif.

Between the source 108 and a detector 130 is one or more shields 124 which prevent or inhibit errant x-rays from reaching the crystals 140 and the detector 130. The arrangement of shields 124 shown in FIG. 1 is exemplary and other shielding layouts are contemplated. The shields 124 may comprise lead or any other material(s) capable of absorbing x-ray energy.

After the slits 120, the x-ray path 112 is directed to the crystal array 140. Any type of crystal material may be utilized that meets the Bragg condition and the ability of the crystal and the crystal alignment to reflect the x-rays of interest. Two or more crystals may be used in the array 140, as will be described in more detail below. In this embodiment, the crystal array 140 comprises germaniums crystals having a high Miller index, such as Ge (9,7,3), or Ge (11,3,3). The alignment of the crystals is such that the angle $\theta_B$ is generally between 80 degrees and 90 degrees.

After reflection or re-direction of the x-rays of interest from the crystal array 140, the x-rays are presented to a filter 154. Multiple filters may be present when multiple x-ray paths 112 exist. An x-ray filter is a device to block or filter out some or all wavelengths or energy bands in the x-ray spectrum. The filter 154 may be placed before or after the crystals 140. The filter 154 may be configured to allow only a single X-ray wavelength to penetrate to the crystals 140 or from the crystals 140. The filter 154 may also be selected based on scattering and the diffraction distance. In this configuration the filter is a Cu (copper) based filter but in other embodiments or configurations other filters types or materials may be adopted for use.

A detector 130 receives the x-rays that pass through the filter 114 along the x-ray path 112. The detector 130 may comprise any type detector capable of capturing and recording x-ray emissions. In one configuration the detector 130 is capable of x-ray imaging. The detector 130 may comprise but is not limited to an image plate, a CCD or CMOS camera, film, photographic film, a gated micro channel plate detector, which is similar to CCD but with rapid action gates, or any other type detector capable detecting x-rays of interest. More than one detector 130 may be provided when multiple x-ray paths exist.

In certain embodiments a processing device 160, such as a computer or specialized electronics, connects to the detector to receive an electrical signal indicating or representing x-ray data. The processing device 160 may process the data to form an image, which may be printed or displayed on a display or screen 168. A memory 164 is provided and stores machine readable code in a non-transitory state that is executable by the processing device to perform the analysis of the data from the detector 130. The memory 154 may also store the data.

Figure 2:
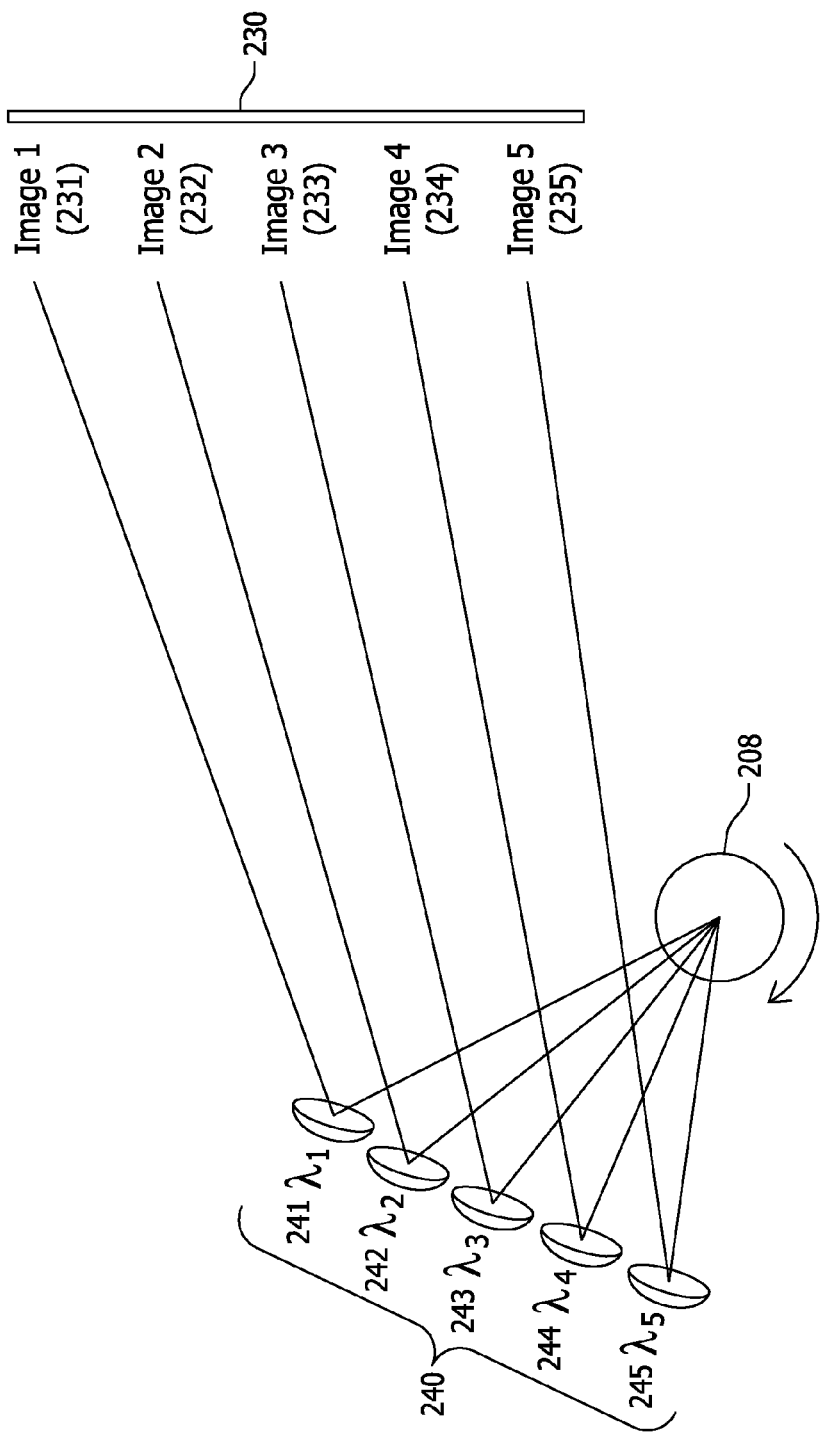
FIG. 2 is a schematic diagram of an exemplary crystal array and detector, according to one embodiment.

FIG. 2 is a schematic diagram of an exemplary crystal array and detector, according to one embodiment. In FIG. 2, an array of crystals 240 is shown that reflect x-rays from a plasma 208 towards a detector 230. The array of crystals 240 includes near-normal-incidence crystals that can provide high-brightness, large solid-angle, and quasi-monochromatic x-ray images. Several crystals may be arranged and tuned to different center wavelengths within a profile of a predetermined emission line to produce a multi-spectral image. The multi-spectral image maps wavelength shift to line-of-sight velocities. In this way, the bulk-motional velocities of a plasmas can be imaged and detected.

In the example shown in FIG. 2, five crystals 241, 242, 243, 244, and 245 are arranged to reflect different center wavelengths of a predetermined emission line. In other words, the crystals are tuned to bandwidths that correspond to very narrow regions of wavelengths within a given emission line. The combination of the wavelengths of each of the crystals in the array 240 are configured to encompass with width of the predetermined emission line. It is preferable to tune the crystal's narrow emission lines being emitted from the plasma 208. While five crystals are shown in FIG. 2, any number of crystals may be used. The number of crystals used provides different resolutions of the bandwidths reflected by the crystal array 240. Further, the placement of the crystals within the array 240 may be adjusted as desired. However, to avoid parallax complications, the crystals should be arranged (closely or in an array) to obtain a similar line of sight as other crystals in the array 240.

Figure 3:
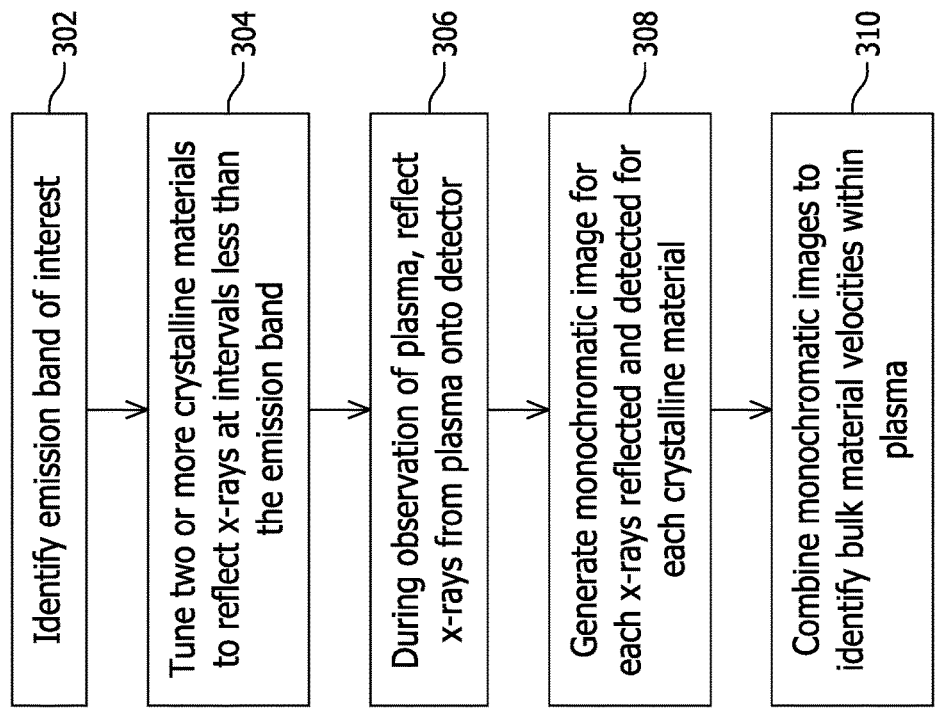
FIG. 3 shows an exemplary method for imaging bulk motional velocities, according to one exemplary embodiment.

FIG. 3 shows an exemplary method for imaging bulk motional velocities, according to one exemplary embodiment. In the description below corresponding to FIG. 3, a specific exemplary configuration will be described to aid in understanding. However, many other configurations may be used depending on the application and the plasma of interest to be imaged.

First, in step 302, an emission band of interest emanating from the plasma is identified. In one example, the above described system is used to detect bulk motional velocities in an implosion plasma, or any other type of plasma or x-ray emitting event. In this example, the emission band to be observed is a Ge He-alpha $^1P_1$ emission line having an upper state component centered about a wavelength of $\lambda$=1.2061 Å. In other embodiments, other emission lines may be studied.

In step 304, two or more crystals in the crystal array are tuned to reflect x-rays at intervals less than a width of the emission band of interest. In the present example, the crystal array 240 is comprised of Quartz crystals having the following properties: miller indices of 0 7 1, 2d=1.2067827 Å, $\Delta\theta$=28.2 μrad at $\lambda$=1.2061 Å, $R_p$=0.9, and (E/$\Delta$E=1.05× $10^6$). The crystals are configured with a 2.8 mm square aperture at an object distance of p=200 mm, operating at 31× magnification. In other embodiments, other crystal types and tunings may be utilized.

In this setup, the emission line is thermal Doppler broadened with $T_i$=4 keV ($\Delta$E=5.9 eV FWHM Gaussian). The object being observed in this instance is a rotating core of implosion plasma 40 μm in diameter, with a exemplary velocity at R=20 μm of 120 μm/ns. As mentioned above, the crystals in the array 240 are tuned to about the center wavelength of the emission line. In this setup, the crystal 241 is tuned to a central wavelength of $\lambda_1$=1.2056177 Å, the crystal 242 is tuned to a central wavelength of $\lambda_2$=1.2058588 Å, the crystal 243 is tuned to a central wavelength of $\lambda_3$=1.2061 Å, the crystal 244 is tuned to a central wavelength of $\lambda_4$=1.2063412 Å, and the crystal 245 is tuned to a central wavelength of $\lambda_5$=1.2065825 Å to span ±120 μm/ns shifts. This corresponds to an angle $\theta_B$ (see FIG. 1) of 87.482, 87.76, 88.07, 88.45, and 88.96 degrees for the crystals in the array 240, respectively. The meridional plane of plane of all of the crystals should preferably be set to be the equatorial plane of the rotating plasma to avoid parallax complications. In other embodiments, other numeric values will be present.

In step 306, the crystals in the crystal array 240 reflect the x-rays onto a detector 230. As explained above, the detector may comprise any suitable configuration including film, an image sensor such as a CCD or CMOS sensor, and the like, or any detector sensor that will detect the present of x-rays. The x-rays captured by the detector 230 are used to create at least one monochromatic image for each of the crystalline reflectors used in the crystal array 240. In this example, five monochromatic images 231, 232, 233, 234, 235 are detected on the detector 230 that correspond to x-rays reflected by the five crystals 241, 242, 243, 244, 245, respectively.

Figure 4A:
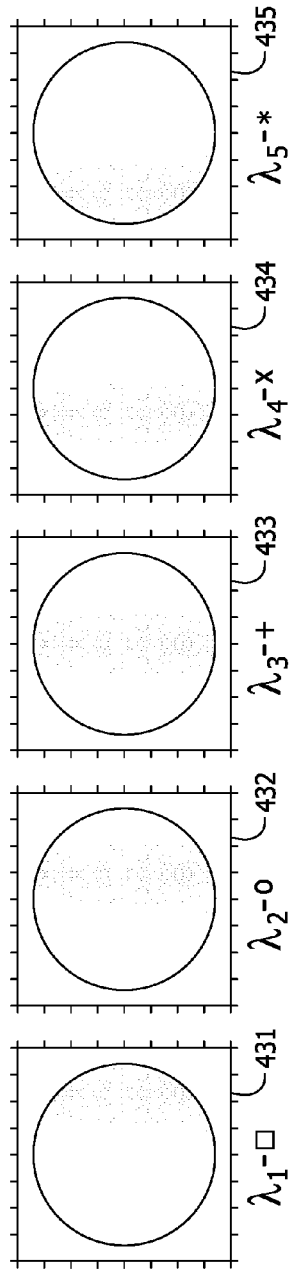
FIG. 4A shows a number of monochromatic images representing material velocities according to embodiment.

FIG. 4A shows a number of monochromatic two-dimensional images 431, 432, 433, 434, 435 generated on the detector 230. In the example embodiment, providing a separate detector for each x-ray path results in the five detector outputs as shown in FIG. 4A. The plasma emits x-rays of many different wavelengths $\lambda_1$ through $\lambda_5$. All of the wavelengths strike the crystal array. Each crystal is designed, selected or tuned to a different x-ray wavelength thereby only reflecting a particular wavelength of x-ray from the group of x-rays which strike a crystal. As shown in FIGS. 2 and 4A, the reflection from is focused to a point on the detector. The particular x-rays which are reflected from a particular crystal strike a detector as shown in FIG. 4A such that each crystal's reflection is shown in a different detector. Association between x-ray wavelength and an associated detector are established thereby mapping the x-ray wavelength to a detector. As shown, the pattern on the detector shows where the x-rays strike the detector and the presence, location, density, and pattern of the x-rays of a particular wavelength. In one embodiment, all the crystals reflect the same wavelength and movement of that wavelength can be tracked over time if the detectors are placed at different locations or the x-rays are otherwise adjusted for time. In one embodiment the crystals reflect different wavelengths thereby disclosing the location of each wavelength of x-ray in the plasma based on where the x-rays strike the detector.

Different wavelengths of the x-rays striking the crystal may be due to movement of the plasma that is emitting the x-rays. This is known as Doppler shift. This allows the data from each detector to correlate to movement of the plasma. For example, if it is known that the wavelength for a stationery plasma, then shift up or down in wavelength reveal motion information.

The monochromatic images, which are two-dimensional, correspond to the wavelengths reflected onto the detector 230 by the crystals in the crystal array 240. As shown in FIG. 4A, the monochromatic images 431, 432 generated by the crystals tuned to wavelengths shorter than the center wavelength of the emission band of interest ($\lambda_1$ and $\lambda_2$) show concentrations of detected x-rays skewed towards the right. The monochromatic images 434, 435 generated by the crystals tuned to wavelengths longer than the center wavelength of the emission band of interest ($\lambda_4$ and $\lambda_5$) show concentrations of detected x-rays skewed towards the left.

From these two-dimensional images 431-435, based on the Doppler effect, it can be seen that the area of the core of the plasma 208 shown in the images 431, 432 is moving towards the crystal array 240, while the area of the core of the plasma 208 shown in the images 434, 435 is moving away from the crystal array 240. Thus, each two-dimensional image 431-435 represents the area of the plasma being imaged and the detector strikes (dots on each image 431-435) represent x-rays emitted from the plasma at the particular wavelength that is reflected by a particular crystal, for example, wavelengths $\lambda_1$ through $\lambda_5$.

Returning to FIG. 3, in step 310, the monochromatic images are combined to identify bulk material velocities within the plasma being observed. The monochromatic images 431-435 are each coded and overlaid against one another to create a final image mapping the velocities within the plasma. For example, each of the monochromatic images may be color-coded. In one instance, the results from image 431 may be coded blue, the results from image 432 may be coded green, the results from image 433 may be coded yellow, the results from image 434 may be coded orange, and the results from image 435 may be coded red. The resulting combined image would thus show by color which portions of the plasma are moving towards the crystal array 240, and which portions are moving away from the crystal array 240.

Figure 4B:
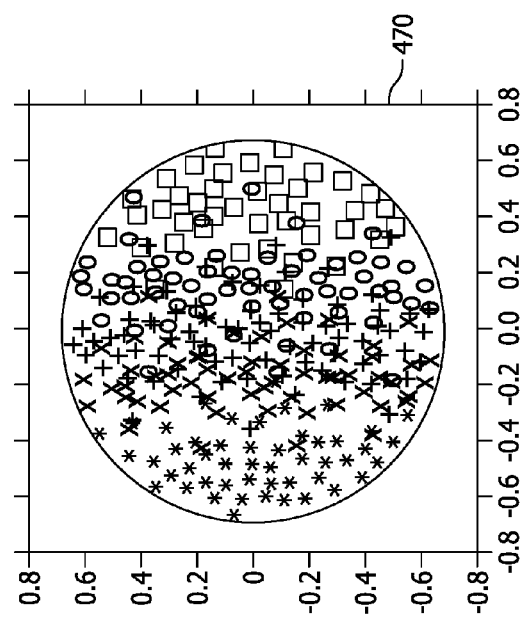
FIG. 4B shows a combined image of material velocities according to one embodiment.

FIG. 4B shows a combined two-dimensional image of material velocities according to one embodiment.

In FIG. 4B, when color is unavailable, the two dimensional images 431-435 may be coded differently to produce the combined image 470. In this example, the results from image 431 are coded with a square symbol (□), the results from image 432 are coded with a circular symbol (○), the results for image 433 are coded with a plus symbol (+), the results from image 434 are coded with an x symbol (x), and the results from image 435 are coded with an asterisk symbol (*). The code represents the wavelength of the reflected x-ray. The combined two-dimensional image 470 thus shows which areas of the plasma 208 are moving towards the crystal array 240, and which areas are moving away from the crystal array 240. The coded image 470 in FIG. 4B may also be representative of the color coded image described above.

Other modifications are also possible. For example, while five crystalline reflectors are used in the above example, less than or greater than five reflectors may be used. Additional detectors may be used, such as one detector for each wavelength. The number of reflectors is dependent on the intervals of wavelengths within an emission band desired for a particular application. Further, more than one crystal array may be used to observe a plasma. For example, a first crystal array may be configured at a first orientation with respect to the plasma, and a second crystal array may be configured at a second orientation with respect to the plasma. This allows imaging of velocities within the plasma to take place from different angles, providing a more detailed understanding of the material velocities throughout the plasmas, such as a three-dimensional view of velocities within the plasmas.

In another modification, the system is configured to capture multiple images over a period of time. In this manner, the change in velocities can observed. In other embodiments, the detector may output video information (a series of images close in time together) to the processor.

It is contemplated that the data processing and interface with the detector may be performed using the exemplary computing elements described below and illustrated in FIG. 5. The computing elements may be established as part of a network or as a stand-alone system.

Figure 5:
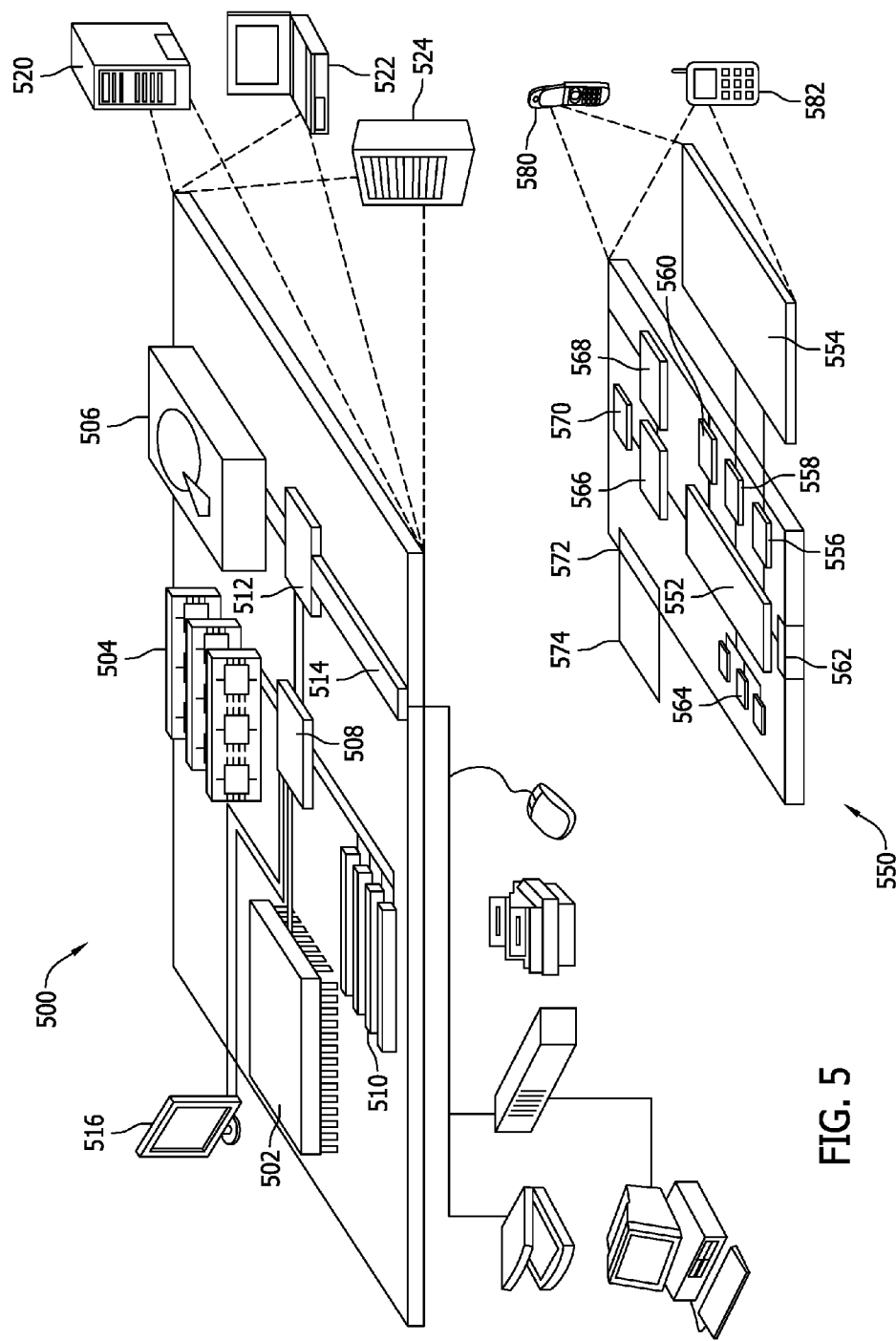
FIG. 5 is a block diagram showing example or representative computing devices and associated elements.

FIG. 5 is a block diagram showing example or representative computing devices and associated elements that may be used to implement the systems method and apparatus described herein. FIG. 5 shows an example of a generic computing device 500 and a generic mobile computing device 550, which may be used with the techniques described here. Computing device 500 is intended to represent various forms of digital computers, such as laptops, desktops, workstations, personal digital assistants, servers, blade servers, mainframes, and other appropriate computers. Computing device 550 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 500 includes a processor 502, memory 504, a storage device 506, a high-speed interface or controller 508 connecting to memory 504 and high-speed expansion ports 510, and a low-speed interface or controller 512 connecting to low-speed bus 514 and storage device 506. Each of the components 502, 504, 506, 508, 510, and 512, are interconnected using various busses, and may be mounted on a common motherboard or in other manners as appropriate. The processor 502 can process instructions for execution within the computing device 500, including instructions stored in the memory 504A or on the storage device 506 to display graphical information for a GUI on an external input/output device, such as display 516 coupled to high-speed controller 508A. In other implementations, multiple processors and/or multiple buses may be used, as appropriate, along with multiple memories and types of memory. Also, multiple computing devices 500 may be connected, with each device providing portions of the necessary operations (e.g., as a server bank, a group of blade servers, or a multi-processor system).

The memory 504 stores information within the computing device 500. In one implementation, the memory 504 is a volatile memory unit or units. In another implementation, the memory 504 is a non-volatile memory unit or units. The memory 504 may also be another form of computer-readable medium, such as a magnetic or optical disk.

The storage device 506 is capable of providing mass storage for the computing device 500. In one implementation, the storage device 506 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 504, the storage device 506, or memory on processor 502.

The high-speed controller 508 manages bandwidth-intensive operations for the computing device 500, while the low-speed controller 512 manages lower bandwidth-intensive operations. Such allocation of functions is exemplary only. In one implementation, the high-speed controller 508 is coupled to memory 504, display 516 (e.g., through a graphics processor or accelerator), and to high-speed expansion ports 510, which may accept various expansion cards (not shown). In the implementation, low-speed controller 512 is coupled to storage device 506 and low-speed bus 514. The low-speed bus 514, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. It may also be implemented as part of a rack server system 524. In addition, it may be implemented in a personal computer such as a laptop computer 522. Alternatively, components from computing device 200A may be combined with other components in a mobile device (not shown), such as device 550. Each of such devices may contain one or more of computing device 500, 550, and an entire system may be made up of multiple computing devices 500, 550 communicating with each other.

Computing device 550 includes a processor 552, memory 564, an input/output device such as a display 554, a communication interface 566, and a transceiver 568, among other components. The device 550 may also be provided with a storage device, such as a microdrive or other device, to provide additional storage. Each of the components 550, 552, 564, 554, 566, and 568, are interconnected using various buses, and several of the components may be mounted on a common motherboard or in other manners as appropriate.

The processor 552 can execute instructions within the computing device 550, including instructions stored in the memory 564. The processor may be implemented as a chipset of chips that include separate and multiple analog and digital processors. The processor may provide, for example, for coordination of the other components of the device 550, such as control of user interfaces, applications run by device 550, and wireless communication by device 550.

Processor 552 may communicate with a user through control interface 558 and display interface 556 coupled to a display 554. The display 554A may be, for example, a TFT LCD (Thin-Film-Transistor Liquid Crystal Display) or an OLED (Organic Light Emitting Diode) display, or other appropriate display technology. The display interface 556 may comprise appropriate circuitry for driving the display 554 to present graphical and other information to a user. The control interface 558 may receive commands from a user and convert them for submission to the processor 552. In addition, an external interface 562 may be provided in communication with processor 552, so as to enable near area communication of device 550 with other devices. External interface 562 may provide, for example, for wired communication in some implementations, or for wireless communication in other implementations, and multiple interfaces may also be used.

The memory 564 stores information within the computing device 550. The memory 564 can be implemented as one or more of a computer-readable medium or media, a volatile memory unit or units, or a non-volatile memory unit or units. Expansion memory 574A may also be provided and connected to device 550A through expansion interface 572, which may include, for example, a SIMM (Single In Line Memory Module) card interface. Such expansion memory 574 may provide extra storage space for device 550, or may also store applications or other information for device 550. Specifically, expansion memory 574 may include instructions to carry out or supplement the processes described above, and may include secure information also. Thus, for example, expansion memory 574 may be provide as a security module for device 550, and may be programmed with instructions that permit secure use of device 550. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 564, expansion memory 574, or memory on processor 552, that may be received, for example, over transceiver 568 or external interface 562.

Because the system may be located in a environmentally challenging environment, the device 550 may communicate wirelessly through communication interface 566, which may include digital signal processing circuitry where necessary. Communication interface 566A may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 568. In addition, short-range communication may occur, such as using a Bluetooth, Wife, or other such transceiver (not shown). In addition, GPS (Global Positioning system) receiver module 570 may provide additional navigation- and location-related wireless data to device 550, which may be used as appropriate by applications running on device 550.

Device 550 may also communicate audibly using audio codec 560, which may receive spoken information from a user and convert it to usable digital information. Audio codec 560 may likewise generate audible sound for a user, such as through a speaker, e.g., in a handset of device 550. Such sound may include sound from voice telephone calls, may include recorded sound (e.g., voice messages, music files, etc.) and may also include sound generated by applications operating on device 550.

The computing device 550 may be implemented in a number of different forms, as shown in the figure. For example, it may be implemented as a cellular telephone 580. It may also be implemented as part of a smart phone 582, personal digital assistant, a computer tablet, or other similar mobile device.

Thus, various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system (e.g., computing device 500 and/or 550) that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In the example embodiment, computing devices 500 and 550 are configured to receive and/or retrieve electronic documents from various other computing devices connected to computing devices 500 and 550 through a communication network, and store these electronic documents within at least one of memory 504, storage device 506, and memory 564. Computing devices 500 and 550 are further configured to manage and organize these electronic documents within at least one of memory 504, storage device 506, and memory 564 using the techniques described herein.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

Also, the particular naming of the components, capitalization of terms, the attributes, data structures, or any other programming or structural aspect is not mandatory or significant, and the mechanisms that implement the invention or its features may have different names, formats, or protocols. Further, the system may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead performed by a single component.

Some portions of above description present features in terms of algorithms and symbolic representations of operations on information. These algorithmic descriptions and representations may be used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "identifying" or "displaying" or "providing" or the like, refer to the action and processes of a computer system, or similar electronic computing device, that manipulates and transforms data represented as physical (electronic) quantities within the computer system memories or registers or other such information storage, transmission or display devices.

Based on the foregoing specification, the above-discussed embodiments of the invention may be implemented using computer programming or engineering techniques including computer software, firmware, hardware or any combination or subset thereof. Any such resulting program, having computer-readable and/or computer-executable instructions, may be embodied or provided within one or more computer-readable media, thereby making a computer program product, i.e., an article of manufacture, according to the discussed embodiments of the invention. The computer readable media may be, for instance, a fixed (hard) drive, diskette, optical disk, magnetic tape, semiconductor memory such as read-only memory (ROM) or flash memory, etc., or any transmitting/receiving medium such as the Internet or other communication network or link. The article of manufacture containing the computer code may be made and/or used by executing the instructions directly from one medium, by copying the code from one medium to another medium, or by transmitting the code over a network.

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

What is claimed is:

1. A system for detecting bulk motional velocities in a plasma, the system comprising:
   a crystal array comprising at least two crystalline reflectors which provide multiple lines of sight for multiple wavelength bands, each reflector tuned to reflect x-rays of a particular wavelength within a single emission band from the plasma to a single point focus to create reflected x-rays;
   at least one detector configured to receive reflected x-rays and generate detector output data, the detector output data being combinable to represent a two-dimensional representation of bulk material velocity of the plasma; and
   a processing device including at least one memory and a display, the processing device configured to execute machine readable instructions stored on the memory, which when executed, cause the system to:
      receive detector output data from the detector, the detector output data comprising information for monochromatic images corresponding to x-rays reflected by the at least two crystalline reflectors; and
      process the detector output data to individually code the monochromatic images and overlay the monochromic images to produce a composite image, the composite image showing Doppler shifts within the single emission band.

2. The system according to claim 1, wherein the at least one detector comprises film.

3. The system according to claim 1, wherein the at least one detector comprises an image sensor.

4. The system according to claim 1, wherein an angle defined by one of the at least two crystalline reflectors and an x-ray path reflected from a crystalline reflector to the at least one detector is between 80 and 90 degrees.

5. The system according to claim 1, further comprising at least one shield disposed between the plasma being observed and the at least one detector.

6. The system according to claim 1, further comprising:
   a collimator configured to narrow a beam of the x-rays that are reflected by the crystal array;
   slits configured to control the divergence of the x-rays; and
   at least one filter configured to block or filter out one or more wavelengths or energy bands in the x-ray spectrum.

7. A method for detecting bulk motional velocities in a plasma, the method comprising:
   identifying a predetermined x-ray emission band emanating from the plasma;
   tuning two or more crystalline reflectors within a crystal array to reflect x-rays within the predetermined emission band, to a single point focus;
   using the two or more crystalline reflectors reflecting the x-rays from the plasma onto a detector to form a two-dimensional image on the detector representing a two-dimensional area of the plasma, each detector configured to focus to a single point focus, the detector comprising one or more detectors;
   generating monochromatic two-dimensional images corresponding to the x-rays reflected by each of the two or more crystalline reflectors to create two or more monochromatic two-dimensional images; and
   combining the two or more monochromatic two-dimensional images into a composite image to identify bulk motional velocities within the plasma.

8. The method of claim 7, wherein the two or more crystalline reflectors have a bandpass that is narrow compared with a Doppler profile of the emission band.

9. The method of claim 7, wherein the crystalline reflectors are near-normal-incidence crystals.

10. The method of claim 7, wherein the detector comprises at least one of an image plate, a CCD camera, film, photographic film, or a gated micro channel plate detector.

11. The method of claim 7, wherein the combining step comprises color coding the monochromatic images such that each monochromatic image is represented by a different color.

12. The method of claim 7, wherein two or more crystal reflectors reflect x-rays emanating from the plasma at different orientations with respect to the plasma.

13. The method of claim 7, wherein a meridional plane of plane of the crystalline reflectors is set at the equatorial plane of the plasma.

14. A system for detecting bulk motional velocities in a plasma, the system comprising:
   a crystal array tuned to reflect x-rays having a predetermined emission line to a point focus, such that at least two crystals in the array are configured to reflect x-rays of a different wavelength to form a two-dimensional;

one or more detectors configured to detect x-rays reflected from the crystal array and receive the two-dimensional image reflected from the crystal array;

one or more shields configured to block the one or more detectors from x-rays emanating directly from the plasma;

a processor configured to receive two-dimensional image information from the one or more detectors, the two-dimensional image information comprising monochromatic images of the x-rays reflected by the crystal array, the processor further being configured to combine the monochromatic two-dimensional images into a composite two-dimensional image showing Doppler shifts within the emission line, such that different x-ray wavelengths are represented in the composite two-dimensional image as different monochromatic colors.

15. The system of claim 14, wherein the crystal array comprises two or more crystalline reflectors tuned to different center wavelengths about a center wavelength of a profile of the predetermined emission line.

16. The system of claim 14, wherein the composite image is a color coded image of the monochromatic images overlaid on top of each other.

17. The system of claim 14, wherein an angle defined by the one of the crystalline reflectors and an x-ray path reflected from the one crystalline reflector to the one or more detectors is between 80 and 90 degrees.

18. The system of claim 14, further comprising:

a collimator configured to narrow a beam of the x-rays that are reflected by the crystal array;

slits configured to control the divergence of the x-rays; and at least one filter configured to block or filter out one or more wavelengths or energy bands in the x-ray spectrum.

* * * * *